(12) United States Patent
Harfensteller et al.

(10) Patent No.: US 8,349,391 B2
(45) Date of Patent: Jan. 8, 2013

(54) RADIUM TARGET AND METHOD FOR PRODUCING IT

(75) Inventors: Mark Harfensteller, Munich (DE); Ernst Huenges, Garching (DE); Michael Schilp, Regensburg (DE); Josue Manuel Moreno Bermudez, Ismaning (DE)

(73) Assignee: Actinium Pharmaceuticals Inc., Florham Park, NJ (US)

( * ) Notice: Subject to any disclaimer, the term of this patent is extended or adjusted under 35 U.S.C. 154(b) by 665 days.

(21) Appl. No.: 11/589,551

(22) Filed: Oct. 30, 2006

(65) Prior Publication Data
US 2007/0153954 A1 Jul. 5, 2007

Related U.S. Application Data (63) Continuation of application No. PCT/EP2005/002619, filed on Mar. 11, 2005.

(30) Foreign Application Priority Data

May 5, 2004 (DE) .......................... 10 2004 022 200

(51) Int. Cl.
*A61M 36/14* (2006.01)
(52) U.S. Cl. ...... 427/5; 427/372.2; 427/402; 427/421.1; 427/424; 427/427.3; 427/521
(58) Field of Classification Search ........... 427/5, 372.2, 427/402, 421.1, 424, 521, 427.3
See application file for complete search history.

(56) References Cited

U.S. PATENT DOCUMENTS

| | | | | |
|---|---|---|---|---|
| 2,442,617 A | * | 6/1948 | Rosenblum | 205/80 |
| 2,554,649 A | | 5/1951 | Tompkins | |
| 2,632,763 A | | 3/1953 | Hagemann | |
| 3,351,049 A | * | 11/1967 | Lawrence | 600/8 |
| 3,750,653 A | * | 8/1973 | Simon | 600/6 |

(Continued)

FOREIGN PATENT DOCUMENTS
DE 103 47 459 B3 5/2005
(Continued)

OTHER PUBLICATIONS

Haissinsky, M.J., "Electrolyse de sels de baryum st de radium dans l'acetone," ("Electrolysis of salts of barium and radium in acetone") Chim. Phys. 34, 321 (with English translation of summary), File: Feb. 5, 2006.

(Continued)

*Primary Examiner* — Elena T Lightfoot
(74) *Attorney, Agent, or Firm* — Wilmer Cutler Pickering Hale and Dorr LLP (57) ABSTRACT

The present invention refers to a method for producing a radium target for the production of radionuclides by means of accelerated protons, whereby at least one radium containing material out of an aqueous-organic solution or suspension of such a material is applied by means of a dispersing device on a surface in such a way that the dispersing device and the surface are moving relatively towards each other and that the solvent is removed substantially spontaneously. Further, the invention refers to a radium target that is created in such a way that it may exhibit an activity of up to 1.5 curie. The radium targets according to the present invention serve for the production of the radionuclide $^{225}$Ac, which may be used in nuclear medicine in the treatment of cancer, particularly in form of its daughter nuclide $^{213}$Bi.

44 Claims, 2 Drawing Sheets

U.S. PATENT DOCUMENTS

| | | | |
|---|---|---|---|
| 4,293,617 A | 10/1981 | Nagy | |
| 4,454,106 A | 6/1984 | Gansow et al. | |
| 4,514,266 A | 4/1985 | Cole et al. | |
| 4,548,790 A | 10/1985 | Horwitz et al. | |
| 4,663,129 A | 5/1987 | Atcher et al. | |
| 4,895,633 A | 1/1990 | Seto et al. | |
| 5,002,885 A | 3/1991 | Stavrianopoulos | |
| 5,085,834 A | 2/1992 | Lemaire et al. | |
| 5,246,691 A | 9/1993 | Geerlings et al. | |
| 5,355,394 A | 10/1994 | van Geel et al. | |
| 5,445,720 A | 8/1995 | Sypula et al. | |
| 5,607,591 A | 3/1997 | Dozol et al. | |
| 5,707,528 A | 1/1998 | Berry | |
| 5,809,394 A | 9/1998 | Bray et al. | |
| 5,863,439 A | 1/1999 | Dietz et al. | |
| 5,885,465 A | 3/1999 | Bray et al. | |
| 6,092,889 A * | 7/2000 | Nakamoto et al. | 347/55 |
| 6,299,666 B1 * | 10/2001 | Apostolidis et al. | 75/393 |
| 6,461,433 B1 * | 10/2002 | Carden et al. | 118/688 |
| 6,511,603 B1 | 1/2003 | Dietz et al. | |
| 6,635,234 B1 | 10/2003 | Larsen et al. | |
| 6,676,987 B2 * | 1/2004 | Zhong et al. | 427/2.24 |
| 7,106,438 B2 | 9/2006 | Morrisroe et al. | |
| 7,378,372 B2 | 5/2008 | Sylvester | |
| 2003/0127395 A1 | 7/2003 | Bond et al. | |
| 2003/0194364 A1 | 10/2003 | Bond et al. | |
| 2003/0219366 A1 | 11/2003 | Horwitz et al. | |
| 2005/0211955 A1 | 9/2005 | Meikrantz et al. | |
| 2007/0076834 A1 | 4/2007 | Moreno Bermudez et al. | |
| 2009/0191122 A1 | 7/2009 | Moreno Bermudez et al. | |
| 2010/0104489 A1 | 4/2010 | Kabai et al. | |

FOREIGN PATENT DOCUMENTS

| | | |
|---|---|---|
| DE | 10 2005 043 012.0 | 9/2005 |
| DE | 10 2004 022 200 A1 | 12/2005 |
| DE | 10 2006 042 191 A1 | 7/2007 |
| DE | 10 2006 008 023 A1 | 8/2007 |
| EP | 0443479 B1 | 7/1994 |
| EP | 0752709 A1 | 1/1997 |
| EP | 0752710 A1 | 1/1997 |
| EP | 0962942 A1 | 12/1999 |
| EP | 1 673 492 B1 | 3/2009 |
| JP | 04326096 A | 11/1992 |
| JP | 2002-517005 | 6/2002 |
| JP | 2010502965 | 1/2010 |
| WO | WO-98/55201 | 12/1998 |
| WO | WO 99/62073 | 12/1999 |
| WO | WO-99/63550 A1 | 12/1999 |
| WO | WO-2005/039634 | 5/2005 |
| WO | WO-2005/039647 A2 | 5/2005 |
| WO | WO-2005/105160 | 11/2005 |
| WO | WO-2007/096119 | 8/2007 |
| WO | WO-2008/028664 | 3/2008 |

OTHER PUBLICATIONS

Ingelbrecht, C., et al.: "Improved electrodeposited actinide layers," Nuclear Instruments and Methods in Physics Research, A 397 (1997) 34-38.

Mirzadeh, S., "Generator-produced Alpha-emitters," Appl. Radiat. Isot., vol. 49, No. 4, pp. 345-349, 1998.

Whitehead, N.E., et al.: "Factors Affecting the Electrodeposition of $^{226}$Ra," Journal of Radioanalytical and Nuclear Chemistry, Articles, vol. 160, No. 2 (1992) 447-485.

International Search Report and Written Opinion of International Patent Application No. PCT/EP2005/002619 filed Mar. 11, 2005.

International Search Report and Written Opinion of International Patent Application No. PCT/EP2004/011510, filed Oct. 13, 2004.

Mullen, G. et al., "Preparation of Targets of Np, Pu, Am, Cm and Cf by Electrodeposition from Organic Solutions," Nuclear Instruments and Methods 128 (1975) 425-428.

van der Walt, T.N. et al., "Quantitative Separation of Gallium from other Elements by Cation-Exchange Chromatography," Anal. Chem., 55: 212-216 (1983).

Burnett, W. et al. (1995), "Determination of Radium-228 in Natural Waters Using Extraction Chromatographic Resins." Radioactivity & Radiochemistry. vol. 6, No. 3, p. 36-44.

Chabaux, F. et al., "A new Ra-Ba chromatographic separation and its application to Ra mass-spectrometric measurement in volcanic rocks," Chemical Geology 114 (1994) 191-197.

Geerlings et al., "The feasibility of $^{225}$Ac as a source of α-particles in radioimmunotherapy," Nuclear Medicine Communications 14: 121-125 (1993).

Geerlings, M.W. "Radionuclides for radioimmunotherapy: criteria for selection," Int. J. Biol. Markers, 8: 180-186 (1993).

Hassfjell et al., "The Development of the α-Particle Emitting Radionuclides $^{212}$Bi and $^{213}$Bi, and Their Decay Chain Related Radionuclides, for Therapeutic Applications," Chem. Rev., 101: 2019-2036 (2001).

Huber et al., "Locoregional α-Radioimmunotherapy of Intraperitoneal Tumor Cell Dissemination Using a Tumor-specific Monoclonal Antibody," Clinical Cancer Research (Suppl.) 9:1s-6s (2003).

Jurcic et al., "Target α particle immotherapy for myeloid leukimia," in Blood, 100: 1233-1239 (2002).

Kaspersen, et al., "Cytotoxicity of 213Bi- and 225Ac-immunoconjugates," Nuclear Medicine Communications, 16:468-476 (1995).

Kirby, H.W. et al., "The Radiochemistry of Radium," National Academy of Sciences, National Research Council, Nuclear Science Series, Issued Dec. 1964.

Nikula et al., "Alpha-Emitting Bismuth Cyclohexylbenzyl DTPA Constructs of Recombinant Humanized Anti-CD33 Antibodies: Pharmacokinetics, Bioactivity, Toxicity and Chemistry," J Nucl Med, 40:166-176 (1999).

Rompp Lexikon Chemie 10th Edition, 1997, pp. 1965-1966.

Burnett, W.C. et al., "Determination of Radium-228 in Natural Waters Using Extraction Chromatographic Resins," Radioactivity and Radiochemistry, 6(3): p. 2-25 (Sep. 1995).

Chiarizia, R. et al. "Uptake of Metal Ions by a New Chelating Ion-Exchange Resin. VII. Alkaline Earth Cations" Solvent Extraction and Ion Exchange, 13(6): 1063-1082 (1995).

Gerlach, V.W. et al. "Zeitschrift fur anorganische und allgemeine Chemie" Band 221 (1934), 103-108 (with English Summary).

Gleason, et al., 1980, "An Improved Ion Exchange Procedure for the Separation of Barium from Radium," Ann Arbor Science Publishers Inc., p. 47-50.

Honigschmid, V.O. et al., "Zeitschrift fur anorganische und allgemeine Chemie," Band 221 (1934), 65-82 (with English Summary).

Kabai, E. "Radium purification for cyclotron target preparation for $^{225}$Ac Production": Sep. 11 to Sep. 14, 2005 Dusseldorf, Techische Universitat Munchen, Institut fur Radiochemie, 1-19.

Kabai, E. et al., "Simultaneous determination of radioactive halogen isotopes and $^{99}$Tc," Czechoslovak Journal of Physics, vol. 53, Suppl. A., A181-A188 (2003).

Moon, D.S. et al., "Preconcentration of radium isotopes from natural waters using $MnO_2$ Resin," Applied Radiation and Isotopes 59: 255-262 (2003).

Nelson, F. "Ion Exchange Procedures V. Separation of Barium and Radium," Journal of Chromatography, 16: 403-406 (1964).

Power, W.H. et al. "Separation of Radium and Barium by Ion Exchange Elution," Analytical Chemistry, 31(6):1077-1079 (1959).

Salutsky, M.L. et al., "Radium-Barium Separation Process," Industrial and Engineering Chemistry, pp. 2162-2166 (1955).

Schicha and Schober, 1997 "Nuklearmedizin—CompactLehrbuch," section 2.3.1, pp. 15, Schattauer Gmbh.

Schicha and Schober, 2003 "Nuklearmedizin—Basiswissen and klinische Anwendung," Section 2.3.1, pp. 13-14, Schattauer Gmbh.

Strelow, F.W.E. "Separation of Traces and Large Amounts of Lead from Gram Amounts of Bismuth, Tin, Cadmium, and Indium by Cation Exchange Chromatography in Hydrochloric Acit-Methanol Using a Macroporous Resin," Anal Chem., 57: 2268-2271 (1985).

Tompkins, E.R. "Separation of Radium from Barium by the Use of an Ion-exchange Column Procedure," J. Am. Chem. Soc. 70 (10): 3520-2 (1948).

van der Walt, T.N. et al., "Quantitative Separation of Gallium from other Elements by Cation-Exchange Chromatography," Anal. Chem., 55: 212 (1983).

Wlodzimirska, B. et al. "Preparation of $^{225}$Ac and $^{228}$Ac generators using a cryptomelane manganese dioxide sorbent," Radiochimica Acta, 91:553-556 (2003).

Huber, Roswitha, "Bewertung der lokoregionalen Radioimmuntherapie disseminierter Tumorzellen des diffusen Magenkarzinoms mit einem $^{213}$Bi gekoppelten tumorspezifischen Antikörper im Mausmodell" (Evaluation of a locoregional radioimmunotherapy of disseminated tumor cells of the diffuse gastric carcinoma with a $^{213}$Bi bound tumor specific antibody in the mouse model), doctorate dissertation in the Faculty of Veterinary Medicine submitted to the Ludwig-Maximilians-University of Munich, Jul. 18, 2003 (Summary of Dissertation in English on pp. 108-109).

International Search Report and Written Opinion, International Patent Application No. PCT/EP2007/007788, Apr. 2005.

Apostolidis et al., 2005, "Cyclotron Production of Ac-225 for Targeted Alpha Therapy", Appl. Radiat. Isot., 62:383-387.

Johnson et al., 1998, "A 222Rn Source for Low-Background Liquid Scintillation Detectors", Nucl. Instrum. & Meth. Physics Res., 414: 459-465.

Vrecek et al., 2004, "Determination of 210Pb and 210Po in Sediment and Soil Leachates and in Biological Materials Using a Sr-Resin Column and Evaluation of col. Reuse", 60: 717-723.

Wang, S. et al., "Nuclear Data for Production of Therapeutic Radionuclides," Nuclear Physics Review, vol. 23, No. 1, Mar. 2006, pp. 78-83 (with English translation of abstract).

International Search Report mailed Aug. 8, 2007 for international Patent Application No. PCT/EP2007/001424 (PCT Publication No. WO 2007/096119 A3) (5 pages).

Written Opinion mailed Aug. 8, 2007 for International Patent Application No. PCT/EP2007/001424 (8 pages).

\* cited by examiner

RADIUM TARGET AND METHOD FOR PRODUCING IT

This application is a continuation of International Patent Application No. PCT/EP2005/002619, filed Mar. 11, 2005, which claims the benefit of German Patent Application No. 10 2004 022 200.2, filed May 5, 2004, which are both incorporated by reference in their entireties.

BACKGROUND OF THE INVENTION

Already in 1993, criteria for the selection of radionuclides for immunotherapy with α-emitters and β-emitters were provided for the first time by GEERLINGS (GEERLINGS, M. W. (1993): Int. J. Biol. Markers, 8, 180-186: "Radionuclides for radioimmunotherapy: criteria for selection") where it turned out due to the difference in energy that the amount of α-emitters to be applied may be more than 1000 times lower than that of β-emitters, if a comparable effect is to be achieved.

Moreover, in the work of GEERLINGS 1993 the α-emitting radionuclides $^{225}$Ac and its daughter isotope $^{213}$Bi turned out to be highly promising for the objects of radioimmunotherapy alongside the in principle usable, however relatively poorly available or instable antibody conjugate producing α-emitters: $^{211}$At, $^{255}$Fm, $^{212}$Bi/$^{212}$Pb, $^{224}$Ra, $^{233}$Ra.

SUMMARY OF THE INVENTION

The present invention refers to a method for producing a radium target for the production of radionuclides by means of accelerated protons. Further, the invention refers to a radium target characterized in that it is obtainable according to a method for the production of a radionuclide by means of accelerated protons, characterized in that at least one radium containing material out of at least one aqueous-organic solution or suspension of such a material is applied by means of a dispersing device on a surface in such a way that the dispersing device and the surface are moving relatively towards each other and that the solvent is removed substantially spontaneously. In one embodiment, the surfaces are selected from the group consisting of: metals, particularly aluminium; copper; titanium; gold; gold plated stainless steel; ceramic materials; organic materials; carbon; silicon and silicon carbide as well as mixtures thereof. In one embodiment, the solutions or suspensions of a $^{226}$Ra compound are nitrate, carbonate, chloride or oxide and/or mixtures thereof. In one embodiment, the protons are accelerated by means of a cyclotron or a linear accelerator. In one embodiment, the radionuclide $^{225}$Ac is produced from $^{226}$Ra by means of protons accelerated in a cyclotron. In one embodiment, the method is carried out through wetting the metal surface and/or the applied radium containing layer only one time or repeatedly with the radium containing aqueous solution or suspension, whereby the removal of the solvent takes place by evaporation. In one embodiment, the wetting takes place by dropwise application or by the application of a thin film. In one embodiment, the solvent from the introduced radium containing aqueous-organic solution or suspension is evaporated by heating, in particular by means of IR-rays. In one embodiment, the method is carried out by applying the radium-containing aqueous-organic solution or suspension under reduced pressure, whereby the removal of the solvent takes place by evaporation at a given lowering of the boiling point. In one embodiment, a cylinder-shaped hollow vessel, in particular a beaker- or cup-shaped object is used as metal surface. In one embodiment, the cylinder-shaped hollow vessel exhibits a groove-shaped recess at the outer edge of the surface of its base. In one embodiment, the recess exhibits a depth of approx. 0.5 to 10 mm, in particular 0.5 to 3 mm and a broadness of approx. 5.5 to 10 mm, in particular 1 to 3 mm. In one embodiment, the $^{226}$Ra-containing solution or suspension is applied dropwise. In one embodiment, the drop diameter used lies in the range of approx. 100 to 1000 μm, in particular approx. 200 to 800 μm, preferably approx. 300 to 600 μm, in particular preferably approx. 450 μm. In one embodiment, the radium-containing aqueous-organic solution or suspension is applied from a capillary in such a way that the base of the groove-shaped recess of the cup-shaped object is wetted and thereby the end of the capillary with the overgrowth of the coating is guided along in direction of the overgrowth. In one embodiment, the distance between the capillary and the metal surface and/or the overgrowth is detected and kept at a constant level by means of a sensor, in particular by means of an optical sensor, preferable a scanning sensor for reflected light. In one embodiment, a capillary made from a hydrophobic material, in particular fluorinated polymers, preferably Teflon, more preferably with a stabilizing metal sheath is used. In one embodiment, the aqueous-organic solution or suspension contains at least one alcohol. In one embodiment, the alcohol is selected from the group consisting of: linear and branched $C_1$ to $C_5$ alkyl alcohols; ethanol, propanol-1, propanol-2, acetone as well as mixtures thereof. In one embodiment, the radium containing layers are formed on the surface of an intermediate support, in particular on the surface of one being made of aluminium foil. In one embodiment, the intermediate support can be placed in the cylinder-shaped hollow vessel. In one embodiment, the radium containing layers on the surface are dried additionally, preferably by means of IR radiation. In one embodiment, the crystal water of the overgrowth is at least largely removed. In one embodiment, the method is carried out continuously. In one embodiment, the method is carried out under an inert gas atmosphere.

Further, the invention refers to an apparatus for carrying out the method for producing a radium target for the production of a radionuclide by means of accelerated protons, characterized in that at least one radium containing material out of at least one aqueous-organic solution or suspension of such a material is applied by means of a dispersing device on a surface in such a way that the dispersing device and the surface are moving relatively towards each other and that the solvent is removed substantially spontaneously. In one embodiment, the surfaces are selected from the group consisting of: metals, particularly aluminium; copper; titanium; gold; gold plated stainless steel; ceramic materials; organic materials; carbon; silicon and silicon carbide as well as mixtures thereof. In one embodiment, the solutions or suspensions of a $^{226}$Ra compound are nitrate, carbonate, chloride or oxide and/or mixtures thereof. In one embodiment, the protons are accelerated by means of a cyclotron or a linear accelerator. In one embodiment, the radionuclide $^{225}$AC is produced from $^{226}$Ra by means of protons accelerated in a cyclotron. In one embodiment, the method is carried out through wetting the metal surface and/or the applied radium containing layer only one time or repeatedly with the radium containing aqueous solution or suspension, whereby the removal of the solvent takes place by evaporation. In one embodiment, the wetting takes place by dropwise application or by the application of a thin film. In one embodiment, the solvent from the introduced radium containing aqueous-organic solution or suspension is evaporated by heating, in particular by means of IR-rays. In one embodiment, the method is carried out by applying the radium-containing aqueous-organic solution or suspension under reduced pressure, whereby the removal of the solvent takes place by evaporation at a given lowering of the boiling point. In one embodiment, a cylinder-shaped hollow vessel, in particular a beaker- or cup-shaped object is used as metal surface. In one embodiment, the cylinder-shaped hollow vessel exhibits a groove-shaped recess at the outer edge of the surface of its base. In one embodiment, the recess exhibits a depth of approx. 0.5 to 10 mm, in particular 0.5 to 3 mm and a broadness of approx. 5.5 to 10 mm, in particular 1 to 3 mm. In one embodiment, the $^{226}$Ra-containing solution or suspension is applied dropwise. In one embodiment, the drop diameter used lies in the range of approx. 100 to 1000 μm, in particular approx. 200 to 800 μm, preferably approx. 300 to 600 μm, in particular preferably approx. 450 μm. In one embodiment, the radium-containing aqueous-organic solution or suspension is applied from a capillary in such a way that the base of the groove-shaped recess of the cup-shaped object is wetted and thereby the end of the capillary with the overgrowth of the coating is guided along in direction of the overgrowth. In one embodiment, the distance between the capillary and the metal surface and/or the overgrowth is detected and kept at a constant level by means of a sensor, in particular by means of an optical sensor, preferable a scanning sensor for reflected light. In one embodiment, a capillary made from a hydrophobic material, in particular fluorinated polymers, preferably Teflon, more preferably with a stabilizing metal sheath is used. In one embodiment, the aqueous-organic solution or suspension contains at least one alcohol. In one embodiment, the alcohol is selected from the group consisting of: linear and branched $C_1$ to $C_5$ alkyl alcohols; ethanol, propanol-1, propanol-2, acetone as well as mixtures thereof. In one embodiment, the radium containing layers are formed on the surface of an intermediate support, in particular on the surface of one being made of aluminium foil. In one embodiment, the intermediate support can be placed in the cylinder-shaped hollow vessel. In one embodiment, the radium containing layers on the surface are dried additionally, preferably by means of IR radiation. In one embodiment, the crystal water of the overgrowth is at least largely removed. In one embodiment, the method is carried out continuously. In one embodiment, the method is carried out under an inert gas atmosphere. In one embodiment, the radium target contains radium within the nanogram range to gram range. In another embodiment, the radium target exhibits an activity of about 1 nCi to 1.5 nCi, preferably approximately 500 mCi of $^{226}$Ra. In one embodiment, the radium target is characterized in that it is present as aluminium beaker or cup, the radium coating being in particular present in ring-shaped form in the area of the groove-shaped recess, preferably on the inside of the outer wall of the aluminium beaker or cup. In one embodiment, the radium target is characterized in that the radium compound that is applied on the surface, in particular on the aluminium surface, is substantially free of support materials, as for example a barium salt. In one embodiment, the radium target is characterized in that it can be sealed waterproof and gasproof. In one embodiment, the radium target is characterized in that it exhibits an aluminium cup with groove-shaped recess and a radium coating being deposited therein, as well as a centrepiece and a ring-shaped cover that can be screwed together therewith, whereby the outer wall of the centrepiece is sealed with an o-ring against the inside of the outer wall of the aluminium beaker and the centrepiece is placed inside of said beaker; and the ring-shaped cover being screwed with the centrepiece, by means of O-ring and stepped ring, which positions the o-ring sealing in axial and radial direction against the inside wall of the centrepiece, so that the target is sealed gasproof and waterproof.

In one embodiment, the apparatus is a device for producing a radium target for the production of a radionuclide by means of accelerated protons, characterized in that at least one radium containing material out of at least one aqueous-organic solution or suspension of such a material is applied by means of a dispersing device on a surface in such a way that the dispersing device and the surface are moving relatively towards each other and that the solvent is removed substantially spontaneously, wherein the device comprises at least one dispersing device with capillary and distance sensor; at least one manipulator device for the realisation of the feed motion of the capillary and the relative movement between capillary and one surface to be coated with radium containing material and/or with a radium containing overgrowth on it; the device being arranged in a casing that is gasproof and shielded against radioactive irradiation and the device containing at least one hatch for locking in and locking out of material.

In particular, the targets according to the present invention are used for the production of radionuclide $^{225}$AC, which is successfully used in nuclear medicine-bound to tumorspecific antibodies—in various clinical trials in the treatment of cancer, particularly in form of its daughter nuclide $^{213}$Bi.

DETAILED DESCRIPTION OF THE INVENTION

One of the fundamental studies for the foundation of a radioimmunotherapy with α-emitters is disclosed in GEERLINGS, M. W., KASPERSEN, F. M., APOSTOLIDIS; C. and VAN DER HOUT, R. (1993): Nuclear Medicine Communications 14, 121-125, "The feasibility of $^{225}$Ac as a source of α-particles in radioimmunotherapy". Here it is described that $^{225}$AC produced from $^{229}$Th and the daughter isotope of $^{225}$AC, namely $^{213}$Bi is suitable as isotope for the radioimmunotherapy with α-emitters. As indications there are described in particular cancer treatment and the treatment of micrometastases of malign tumors using tumor-specific monoclonal antibodies as carriers for α-emitters.

A further study of KASPERSEN, F. M., BOS, E., DOORNMALEN, A. V., GEERLINGS, M. W., APOSTOLIDIS, C. and MOLINET, R. (1995): Nuclear Medicine Communications, 16, 468-476: "Cytotoxicity of $^{213}$Bi- and $^{225}$AC-immunoconjugates" confirms and quantifies the cytotoxic effect of $^{213}$Bi and $^{225}$AC with in vitro tests using the human epidermoid tumor cell line A431.

Moreover, it is suggested to use $^{213}$Bi for the treatment of malignant diseases of the blood system.

Further, in KASPERSEN et al. 1995 a process can be found with which antibodies can be bound chemically to a chelator suitable for $^{213}$Bi and $^{225}$Ac. It has proved that for example p-isothiocyanatobenzyl-diethylentriamine-pentaacetate (benzyl-DTPA) is particularly suitable.

A further chelator, namely cyclohexyl-DTPA is for example described in NIKULA, T. K., McDevitt, M. R., FINN, R. D., WU, C., KOZAK, R. W., GARMESTANI, K., BRECHBIEL, M. W., CURCIO, M. J., PIPPIN, C. G., TIFFANY-JONES, L., GEERLINGS, M. W., Sr., APOSTOLIDIS, C., molinet, r., GEERLINGS, M. W., Jr., Gansow, o. A. And Scheinberg, d.a. (1999): J Nucl. Med, 40, 166-176: "Alpha-Emitting Bismuth Cyclohexylbenzyl DTPA Constructs of Recombinant Humanized Anti-CD33 Antibodies: Pharmacokinetics, Bioactivity, Toxicity and Chemistry".

An overview on the chemistry of chelators is for example to be found in HASSFJELL, S, and BRECHBIEL, W. (2001): Chem. Rev., 101, 2019-2036: "The Development of the α-Particle Emitting Radionuclides $^{212}$Bi and $^{213}$Bi, and Their Decay Chain Related Radionuclides, For Therapeutic Applications"

In the meantime, there are various radioimmunotherapeutic approaches of cancer treatment with $^{225}$Ac and $^{213}$Bi in different stages of clinical trials.

The medical-clinical significance of the present invention may, for example, become apparent from two promising therapeutic approaches:

On the one hand, JURCIC, J. G., LARSON, S. M., SGOUROS, G., McDEVITT, M. R., FINN, R. D., DIVGI, C. R. Åse, M. B, HAMACHER, K. A, DANGSHE, M., HUMM, J. L., BRECHBIEL, M. W., MOLINET, R., SCHEINBERG, D. A. (2002) in Blood, 100, 1233-1239 report a significant therapeutical success in the treatment of patients with acute myelogenous leukaemia (AML) and chronic myelogenous leukaemia (CML) by using $^{213}$Bi, which is bound to HuM195, a formulation of a monoclonal anti-CD33-antibody, which was developed for the humane medicine. This study was the first proof-of-concept where a human being was treated with a systemic radioimmunotherapy comprising an α-emitter, which was transported to a tumorspecific cellular target.

On the other hand, HUBER, R., SEIDL, C., SCHMID, E, SEIDENSCHWANG, S., BECKER; K.-F., SCHUMACHER; C., APOSTOLIDIS, C., NIKULA, T., KREMMER, E., SCHWAIGER, M. and SENEKOWITSCH-SCHMIDTKE, R. (2003): Clinical Cancer Research (Suppl.) 9, 1s-6s: "Locoregional α-Radioimmunotherapy of Intraperitoneal Tumor Cell Dissemination Using a Tumor-specific Monoclonal Antibody" report the therapeutic effectivity of $^{213}$Bi-d9MAB—with low bone marrow toxicity—and the possible application of a locoregional therapy for patients who suffer from gastric carcinoma, who express d9-E-Cadherine.

More results of studies and partial aspects in this matter are shown in: Roswitha HUBER, doctorate dissertation in the Faculty of Veterinary Medicine submitted to the Ludwig-Maximilians-University of Munich, Jul. 18, 2003: "Bewertung der lokoregionalen Radioimmuntherapie disseminierter Tumorzellen des diffusen Magenkarzinoms mit einem $^{213}$Bi gekoppelten tumorspezifischen Antikörper im Mausmodell" (Evaluation of a locoregional radioimmunotherapy of disseminated tumor cells of the diffuse gastric carcinoma with a $^{213}$Bi bound tumor specific antibody in the mouse model).

This dissertation was originated from Nuklearmedizinische Klinik and Poliklinik of the Technical University of Munich, the University hospital "Klinikum rechts der Isar", dean: Prof Dr. M. Schwaiger. The dissertation was prepared under the supervision of Prof. Dr. med. Dr. phil. Reingard Senekowitsch-Schmidtke and was presented to the veterinary faculty via Prof. Dr. med. vet. K. Tempel, Institute for Pharmacology, Toxicology and Pharmacy of the Faculty of Veterenary Medicine of the Ludwig-Maximilians-University of Munich, director: Prof. Dr. med. vet. R. Schulz.

According to HUBER 2003, each year 18 out of 100 000 Germans come down with gastric carcinoma alone. In Japan, even 126 out of 100 000 people are affected. This means about 156 000 incidences per year in Japan alone. There, as well as in China, Taiwan and Korea, gastric carcinoma is one of the most frequent causes of death in consequence of a tumor. When a peritoneal carcinomatosis, the consequence of diffuse expansion of tumor cells in the abdominal cavity, is diagnosed, the life expectancy of a patient is at present about 12 months. Even with resectable gastric carcinoma, this means with carcinoma, which have not yet disseminated and with negative diagnostic findings with respect to lymph nodes, the relapse-free three-year-survival-rate is at about 45%, only.

Up to now the application of cytostatica within a chemotherapy seemed to be the most promising therapeutic way.

However, the side effects range from immunosuppression, coagulopathy, metabolic anoxia, mucositis and hyperuricaemia to the danger of cytostatica induced secondary tumors. Particularly affected is here quickly proliferating tissue as bone marrow and the epithelium of the gastrointestinal tract as well as of the oral mucosa.

The radioimmunotherapy, in contrast, uses protein structures located on the membrane, that are expressed by tumor cell lines in order to bind cytotoxic active substances via a carrier. Mostly, an overexpression of the binding molecule at the tumor cell is central to a radioimmunotherapy. The target molecule for the tumor associated antibodies is thus also expressed to a lower extend in physiologic cells of the organism. This implies that any therapeutic agent for radiotherapy also binds to these cells.

Particularly, in the treatment of acute or chronic myelogenous leukaemia the meaning of the present invention takes effect, namely for the preparation of a suitable α-emitter, namely $^{225}$Ac which forms through decay reaction the daughter nuclide $^{213}$Bi, which exhibits a half-life of about 45 min. and is bound, for example, to a tumorspecific antibody.

The $^{213}$Bi atom decays via a α-decay to $^{213}$Po, which releases its α-decay energy of 8.4 MeV with a period of decay of 4 μs instantly in the tissue within a distance of 80 nm when decaying and thus effectively kills cells in its immediate neighborhood due to its high linear energy transfer.

This so called locoregional application enables a quick binding of the $^{213}$Bi bound tumor specific antibody to the tumor antigenes with maximal therapeutic success and minimal toxicity.

Not before the late 80s was the α-emitter $^{213}$Bi was discovered for radioimmunotherapy and further examined by GEERLINGS 1993. However, in the standard textbook of Schicha and Schober, 1997 "Nuklearmedizin—Basiswissen and klinische Anwendung" (nuclear medicine—basic knowledge and clinical application) it can be read: "The linear energy transfer of α-rays is so big that the likeliness for the creation of irradiation damages is bigger than a therapeutic effect. For this reason, nuclides, which release α-rays, are not applied in the nuclear medicine.". ("Der lineare Energietransfer ist bei α-Strahlen so groß, daß die Wahrscheinlichkeit für die Erzeugung von Strahlenschäden größer ist als ein therapeutischer Effekt. Aus diesem Grunde werden Nuklide, die α-Strahlen emittieren, in der Nuklearmedizin . . . nicht eingesetzt.")

However, in the clinical application of such α-emitters in combination with tumorspecific antibodies, exactly the opposite has proved to be true (cf. JURCIC et al. 2002). Consequently, the question arose which isotope it was best to use and how it could be prepared reliably and continuously.

Most of the over hundred available α-emitters can already be excluded from in vivo application for practical reasons (cf. GEERLINGS 1993). These α-emitters have to meet requirements like sufficient chemical and physical purity, economic availability and an adequate half-life. The latter has to be long enough for binding to the antibodies and for the biologic allocation and has to be short enough so that the patient is not put at an unnecessary risk due to excessive exposition to the rays.

One of the few nuclides which fulfil these criteria (cf. GEERLINGS 1993) is the nuclide pair $^{213}$Bi/$^{213}$Po with a half-life of 45.6 min ($^{213}$Bi). The photon emission with 440 KeV of $^{213}$Bi additionally permits an in vivo scintiscanning of the patient as well as an easy measurement of the activity using an α-ray counter.

Moreover, in radiation safety it is important that the radiation can be detected easily. Furthermore, also traces of further daughter nuclides of $^{225}$Ac/$^{213}$Bi as for example $^{221}$Fr or $^{209}$Pb can be determined by new methods of measurement and can also be included into the dosimetry alongside the quality control.

In the meantime, $^{213}$Bi has become available via the production of $^{225}$AC, for example according to EP 0 752 709 B1 and EP 0 962 942 A1 and particularly via the so called "thorium cow" according to U.S. Pat. No. 5,355,394. However, the production via the above-mentioned "thorium cow" is very expensive, as it derives from an irradiaton of $^{226}$Ra over several years, whereby finally among others an isotope mixture of $^{228}$Th and $^{229}$Th is assembled, whereby $^{229}$Th again decays via $^{225}$Ra into $^{225}$Ac, which decays to $^{213}$Bi.

Thus, the mother-daughter nuclide pair $^{225}$Ac/$^{213}$Bi is available in principle, however, neither in an adequate quantity and continously nor at an acceptable price, however—as mentioned initially—first clinical studies with $^{225}$Ac/$^{213}$Bi conjugated to HuM195, a humanized anti-CD33 monoclonal antibody are very successful against myeloid leukaemia. The first clinical phase I trials with $^{213}$Bi-HuM195 were carried out with excellent therapeutic results at leukaemia patients at the Memorial Sloan-Kettering Cancer Center in New York (JURICIC et al. 2002).

In a cyclotron, the first of which was produced in 1931, electrically charged particles are accelerated on spiral shaped orbits through an electrical high-frequency field.

In particular, protons can be accelerated with the help of a cyclotron having a sufficiently high current to such high energies that they can be used in experimental and applied nuclear physics for isotope production in a quantitative scale.

EP 0 752 709 B1 describes, for example, a method for producing actinium-225 from radium-226, characterized in that protons accelerated in a cyclotron are projected onto a target of radium-226 in a cyclotron, so that the instable compound nucleus $^{222}$AC is transformed into Actinium-225 while emitting two neutrons (p,2n-reaction), whereby after a waiting period, during which the Actinium-226, which has been formed simultaneously due to the emission of only one neutron, decays mostly due to its considerably shorter half-life and Actinium is chemically separated, so that an almost exclusively pure isotope Ac-225 is obtained.

The $^{226}$Ra target used according to the procedure of EP 0 752 709 B1 is not specified in detail there.

EP 0 962 942 A1 also describes a method for producing Ac-225 by irradiation of $^{226}$Ra with protons, which are accelerated in a cyclotron to an energy of 10 to 20 MeV.

According to the prior art of EP 0 962 942 A1, the target nuclide $^{226}$Ra is used in the form of RaCl$_2$, which can be obtained for example by precipitation with concentrated HCl or radiumcarbonate (RaCO$_3$). These radium substances are then pressed into target pellets. Prior to irradiation of the radium salts with protons, the pellets are heated to about 150° C. in order to release crystal water and are then sealed in a silver capsule. The capsule is then mounted on a frame-like support and connected to a water cooling circuit. The target itself exhibits a window, which is arranged in a way that the proton beam hits the target through the window. According to EP 0 962 942 A1, the target exhibits a surface of about 1 cm$^2$.

Although it is already possible to achieve good Actinium-225-yields with the targets according to EP 0 962 942 A1, it has turned out in practice that this target construction can heat itself under certain conditions due to the proton beam in such a way that the silver capsule tears open and thus both destroys the target as well as contaminates the cyclotron and peripheral components.

As a result, it is the object of the present invention to provide improved radium targets for the production of radionuclides by means of accelerated protons, on the basis of the prior art of EP 0 962 942 A1.

With respect to a method, the above object is achieved by a method for producing a radium target for the production of a radionuclide by means of accelerated protons, characterized in that at least one radium containing material out of at least one aqueous-organic solution or suspension of such a material is applied by means of a dispersing device on a surface in such a way that the dispersing device and the surface are moving relatively towards each other and that the solvent is removed substantially spontaneously.

With regard to a radium target, the above object is achieved by a radium target characterized in that it is obtainable according to a method for producing a radium target for the production of a radionuclide by means of accelerated protons characterized in that at least one radium containing material out of at least one aqueous-organic solution or suspension of such a material is applied by means of a dispersing device on a surface in such a way that the dispersing device and the surface are moving relatively towards each other and that the solvent is removed substantially spontaneously. In one embodiment, the surfaces are selected from the group consisting of: metals, particularly aluminium; copper; titanium; gold; gold plated stainless steel; ceramic materials; organic materials; carbon; silicon and silicon carbide as well as mixtures thereof. In one embodiment, the solutions or suspensions of a $^{226}$Ra compound are nitrate, carbonate, chloride or oxide and/or mixtures thereof. In one embodiment, the protons are accelerated by means of a cyclotron or a linear accelerator. In one embodiment, the radionuclide $^{225}$Ac is produced from $^{226}$Ra by means of protons accelerated in a cyclotron. In one embodiment, the method is carried out through wetting the metal surface and/or the applied radium containing layer only one time or repeatedly with the radium containing aqueous solution or suspension, whereby the removal of the solvent takes place by evaporation. In one embodiment, the wetting takes place by dropwise application or by the application of a thin film. In one embodiment, the solvent from the introduced radium containing aqueous-organic solution or suspension is evaporated by heating, in particular by means of IR-rays. In one embodiment, the method is carried out by applying the radium-containing aqueous-organic solution or suspension under reduced pressure, whereby the removal of the solvent takes place by evaporation at a given lowering of the boiling point. In one embodiment, a cylinder-shaped hollow vessel, in particular a beaker- or cup-shaped object is used as metal surface. In one embodiment, the cylinder-shaped hollow vessel exhibits a groove-shaped recess at the outer edge of the surface of its base. In one embodiment, the recess exhibits a depth of approx. 0.5 to 10 mm, in particular 0.5 to 3 mm and a broadness of approx. 5.5 to 10 mm, in particular 1 to 3 mm. In one embodiment, the $^{226}$Ra-containing solution or suspension is applied dropwise. In one embodiment, the drop diameter used lies in the range of approx. 100 to 1000 μm, in particular approx. 200 to 800 μm, preferably approx. 300 to 600 μm, in particular preferably approx. 450 µm. In one embodiment, the radium-containing aqueous-organic solution or suspension is applied from a capillary in such a way that the base of the groove-shaped recess of the cup-shaped object is wetted and thereby the end of the capillary with the overgrowth of the coating is guided along in direction of the overgrowth. In one embodiment, the distance between the capillary and the metal surface and/or the overgrowth is detected and kept at a constant level by means of a sensor, in particular by means of an optical sensor, preferable a scanning sensor for reflected light. In one embodiment, a capillary made from a hydrophobic material, in particular fluorinated polymers, preferably Teflon, more preferably with a stabilizing metal sheath is used. In one embodiment, the aqueous-organic solution or suspension contains at least one alcohol. In one embodiment, the alcohol is selected from the group consisting of: linear and branched $C_1$ to $C_5$ alkyl alcohols; ethanol, propanol-1, propanol-2, acetone as well as mixtures thereof. In one embodiment, the radium containing layers are formed on the surface of an intermediate support, in particular on the surface of one being made of aluminium foil. In one embodiment, the intermediate support can be placed in the cylinder-shaped hollow vessel. In one embodiment, the radium containing layers on the surface are dried additionally, preferably by means of IR radiation. In one embodiment, the crystal water of the overgrowth is at least largely removed. In one embodiment, the method is carried out continuously. In one embodiment, the method is carried out under an inert gas atmosphere.

In particular, the present invention refers to a first method for producing a radium target for the production of radionuclides by means of accelerated protons, whereby at least one radium containing material out of one aqueous-organic solution or suspension of such a material is applied on a surface by means of a dispersing device in such a way that the dispersing device and the surface are moving relatively towards each other and that the solvent is removed substantially spontaneously.

In a cyclotron materials may be altered radiochemically by means of the high-energy ionic current. In order to alter said materials, they have to be integrated in a so called target. The target enters the ionic current and the contained materials are subjected to the ionic current. Extensive cooling devices prevent the overheating of the target.

In the course of the development of a production device for cyclotron targets, radioactive material, as for example radium, has, among others, to be introduced in a cup-shaped object. Radium is very reactive in metallic form. Thus, it is desirable to use radium components.

The general deposition mechanism as proposed works as follows:

A small amount of a liquid containing the matter to be irradiated is dosed either in a cup or on an intermediate carrier, for example an aluminium foil, arranged inside the cup.

Through a physical or chemical reaction the matter to be irradiated is separated from the liquid and a solid and durable layer is formed.

The procedure may be repeated as often as required, until the desired thickness of the layer is obtained.

The target is irradiated in the cyclotron and the desired matter is produced.

After the irradiation, the layer is released from the cup or from the carrier by means of physical or chemical procedures and the desired substances are subsequently separated from the side products.

The deposition procedures used in the present invention are preferable procedures where radioactive compositions or other substances are dissolved or suspended in a solvent, as for example water or isopropyl alcohol. The solvent may then be evaporated very easily by exposure to heat and the radioactive components or other substances remain in form of an solid overgrowth on the surface to be coated.

With the method according to the invention, it is thus possible to deposit any amount of a dissolvable or suspendable radium containing material at the desired positions on a surface.

In addition to this extraordinary big amount, which cannot be obtained with other methods, as for example the electrodeposition method, this method further provides other advantages compared with the methods used up to now:

One approach known is to press the material to be irradiated in the target. In this method, powdery material is introduced into the target and compressed, for example, by means of a pressure piston. One disadvantage is the difficult handling of powdery material, which bears the danger of contamination of the environment if radioactive substances are used, due to the dust that is difficult to handle. If only small amounts of powdery material are used, it may be difficult to compress said small amounts of powdery material, as the volume is very small.

A second approach is a kind of electroplating as described in the parallel German patent application DE 103 47 459.5 filed on Oct. 13, 2003 of the present applicant. If the matter to be irradiated builds iones in the liquid, these can be deposited by the application of an voltage on a conducting material, for example an aluminium foil. A minor disadvantage lies, however, in the fact that this method is a little difficult to carry out, although it works very effectively on principle. Further, the yield is smaller as that of the present invention, which might be due to the fact that the degree of deposition is as a rule reduced with increasing thickness of the layers, which is probably due to changed resistances in the layers that have already been deposited, as well as to the changed surface properties. Another problem may be the introduction of additional carrier material in the irradiation volume that has already been small. In this case, the volume that can be used effectively is further decreased. Additional material forms undesired isotopes due to the irradiation, which may render a further processing of the irradiated material fixed on the support more difficult.

In contrary to a lot of other procedures of the state of the art, it is also possible to coat the inside walls. Particularly at cylinder-shaped targets the coating of overhead surface areas is rendered possible by means of successive rotation. This way, the density of the material to be irradiated may be increased at the outer wall of the target and the effective irradiation volume can be better made use of.

As surfaces for the application of radium containing material, any surface on substances are usable, which do not perform undesired side reactions when being subjected to irradiation with accelerated protons. They are in particular ones selected from the group consisting of: metals, particularly aluminium; copper; titanium; gold; gold plated stainless steel; ceramic materials; organic materials; carbon; silicon and silicon carbide as well as mixtures thereof.

Preferred is a method using a solution or suspension of a $^{226}$Ra salt, in particular nitrate, carbonate, chloride or oxide and/or mixtures thereof. Nitrate has proved to be particularly suitable.

Preferably, the protons are accelerated by means of a cyclotron or a linear accelerator.

Due to the above-described radioimmunotherapeutic use, it is a particularly preferred embodiment of the present invention to prepare the radionuclide $^{225}$Actinium from $^{226}$Radium with the method of the present invention by means of protons accelerated in a cyclotron, in order to provide a continuous source of $^{225}$AC with high yields, that is readily available.

It is preferred that the $^{226}$Radium containing solution or suspension is applied by one-time- or repeated wetting of the applied radium containing layer, whereby the removal of the solvent takes place by vaporizing.

According to the invention, the application of radium containing material on the surface to be coated may take place for example by dropwise application or by the application of a thin film.

On the one hand this may take place by application by means of a fixed dispersing device on a rotating surface, as for example on an aluminium surface.

On the other hand it is also possible to move the dispersing device over the surface that is to be coated.

The advantage of both approaches is, firstly, that hereby uniform layers may be produced. Secondly, the centrifugal force can be utilized in order to apply the layer, for example, on a surface that lies angular to the vector of the centrifugal acceleration.

Moreover, for constructive reasons, it may further be necessary and advantageous to use either one or the other construction method.

A preferred embodiment of the present invention is the application of the radium containing aqueous-organic solution or suspension by dropwise application or by application of a thin film on a heated aluminium surface. Hereby, the solvent vaporizes spontaneously when the surface is sufficiently hot and the drop is sufficiently small or the film is sufficiently thin, respectively, and the radium containing components remain as solid layer. This procedure has the advantage that it can be carried out particularly easily without much technical effort.

A further preferred embodiment is the application of the radium containing aqueous-organic solution or suspension on the surface, for example an aluminium surface and whereby the solvent is evaporated simultaneously by means of IR irradiation. With this method an excellent quality of the surface is obtained in the applied layer.

A further preferred embodiment of the present invention is to carry out the method according to the invention by application of the radium containing aqueous-organic solution or suspension under reduced pressure, whereby the removal of the solvent by means of evaporation takes place at a given reduced boiling point.

The use of a cylinder-shaped hollow vessel, in particular a beaker- or cup-shaped object, as surface has the advantage that the products of the nuclear reaction, in particular $^{225}$Ac may easily be released from the hollow vessel, whereby the danger of contamination is reduced considerably. Aluminium has proved to be particularly suitable in this context.

It is advantageous if the used cylinder-shaped hollow vessel exhibits a groove-shaped recess at the outer edge of the surface of its base. By this recess, firstly, the formed $^{225}$Ac layer may be geometrically exactly defined. Secondly, this embodiment further provides the possibility to arrange the radium containing material in an ideal way in the proton beam to thereby increase the $^{225}$Ac yield at the proton irradiation.

During the carrying out of the present invention in practice, it has proved to be advantageous, if a recess with a depth of approx. 0.5 to 10, in particular approx. 0.5 to 3 mm, and a breadth of approx. 0.5 to 10 mm, in particular 1 to 3 mm, is used.

A preferred technique for the dosed application of the $^{226}$Ra containing solution or suspension is the dropwise application. Of course, the solution may, if required, also be applied in form of a fine haze, for example by spraying.

In practice it has turned out to be advantageous if the drop diameter used lies in the range of approx. 100 to 1000 µm, in particular approx. 200 to 800 µm, preferable approx. 300 to 600 µm, particularly preferable approx. 450 µm.

It has turned out that the wetting of the base, for example by means of a capillary, is a further excellent method for the application of the radium containing aqueous-organic solution or suspension, whereby the end of the capillary is guided corresponding to the overgrowth of the coating along the direction of the overgrowth. With this technique, trapped air that may for example occur by dropwise application, is avoided as far as possible.

Thereby, the surface temperature, in particular the surface temperature of the aluminium used, preferably lies in the range of approx. 40° C. to 100° C., preferable in the range of approx. 60° C. to 90° C., in particular approx. 85° C.

The distance between the capillary and the surface and/or the overgrowth is detected and kept at a constant level by means of a sensor, in particular by means of an optical sensor, preferably a scanning sensor for reflected light. This enables the deposition of an uniform film.

The use of a capillary out of a hydrophobic material, in particular fluorinated polymers, preferably teflon, in particular preferred with a stabilizing metal sheath is further preferred. Hereby, advantages arise due to the favourable alteration of the surface tension of the escaping hydrophilic liquid at the hydrophobic interface and the uniformity of the liquid film that is achieved hereby.

It is advantageous if the aqueous-organic solution or suspension contains at least one alcohol, as hereby the vaporization point of the solvent is reduced.

In this context, it has turned out that the best results for the purposes of the present invention are achieved with an alcohol, selected from the group consisting of: linear and branched $C_1$ to $C_5$ alkyl alcohols; ethanol, propanol-1, propanol-2, acetone as well as mixtures thereof.

As the radium containing layers are fixed in a solid aluminium cup as the cylinder-shaped hollow vessel, it is largely prevented that the formed target layer peels off or flakes off and the danger of contamination can be reduced as radioactive airborne dust may as well be reduced drastically.

In order to facilitate the release of the irradiated layer, it is advisable to insert an intermediate support, for example an aluminium foil, prior to the coating. This way, the coating may be released easily without a fixed connection to the target cup. Furthermore, the intermediate support bars contaminations to creep from the target cup into the coating during the irradiation.

It is further preferred to carry out the method according to the invention in a continuous way, as by doing so, firstly, uniform $^{226}$radium containing layers are obtained and, secondly, targets can be produced at least for short time storage, which is vital for the medicinal-pharmacological application.

Additional drying and even a largely removal of the crystal water may be reasonable in order to lower the water content of the deposited radium containing material, for example by means of IR irradiation. This measure is reasonable, as the crystal water, that would otherwise still be contained in the proton beam, may lead to a swelling of the layer and, thus, to heterogeneities as well as to contaminations.

If necessary, the method according to the invention may be carried out in a preferred embodiment under an inert gas atmosphere.

The radium targets obtainable via the method according to the invention contain $^{226}$radium within the nanogram range to gram range.

The amount of radioactivity in the radium targets according to the invention lies preferable in the range of approx. 1 nCi to 1.5 Ci, preferably approx. 500 mCi of $^{226}$Ra.

The radium targets of the present invention are preferably present in form of aluminium beakers or aluminium cups, whereby the radium coating is in particular present in a ring-shaped form in the area of the groove-shaped recess, preferably on the inside of the outer wall of the aluminium beaker or cup. This has the special advantage of an optimal geometrical positioning within the irradiation window.

According to the method of the present invention, the radium salt of the radium targets is substantially free of carrier materials as for example a barium salt. Thus, the purification after the carrying out of the nuclear reaction becomes substantially more simple, as it is not necessary to separate the $^{225}$Ac salts from any carrier materials.

According to the present invention, it is further preferred to use a solution of a $^{226}$Ra salt, in particular nitrate, as these salts are dissolvable in aqueous-alcoholic solutions, for example in 70 to 90% isopropyl alcohol.

However, also $^{226}$Ra chlorides, $^{226}$Ra carbonates or $^{226}$Ra oxides may be used as a starting material.

A radium target is preferred that can be sealed waterproof as well as gasproof. Firstly, this is necessary, as the target is cooled with water during the irradiation and, secondly, as no gaseous or dust-like reaction products are allowed to leave the target.

An exemplary radium target is characterized in that it exhibits an aluminium cup with groove-shaped recess and a radium coating being deposited therein, as well as a centrepiece and a ring-shaped cover that can be screwed together therewith, whereby the outer wall of the centrepiece is sealed with an o-ring against the inside of the outer wall of the aluminium beaker and the centrepiece is placed inside of said beaker; and the ring-shaped cover being screwed with the centrepiece, by means of o-ring and stepped ring, which positions the o-ring sealing in axial and radial direction against the inside wall of the centrepiece, so that the target is sealed gasproof and waterproof.

Further, the present invention refers to a device for the carrying out of the described method with:
  at least one dispersing device with capillary and distance sensor;
  at least one manipulator device for the realisation of the feed motion of the capillary and the relative movement between capillary and one surface to be coated with radium containing material and/or with a radium containing overgrowth on it;
  the device being arranged in a casing that is gasproof and shielded against radioactive irradiation and the device containing at least one hatch for locking in and locking out of material.

It is a preferred embodiment of the device according to the invention to form it as glovebox, so that it is perfectly usable for the handling of radioactive substances under the conventional safety conditions in the field of radioactivity.

According to the invention, it is preferred that the radio nuclide $^{225}$Ac is produced from $^{226}$Ra by means of protons accelerated in a cyclotron or in a linear accelerator, as with the targets according to the invention it is, for the first time, rendered possible to produce Actinium-225 in a continuous way for the production of radioimmunotherapeutic compounds, as for example $^{225}$Ac-and $^{213}$Bi-labelled antibodies, in particular monoclonal antibodies, for radioimmunotherapy of cancer and metastases.

These radioimmunochemic methods are, for example, summarized nuclearchemically as well as clinically in the doctorate dissertation von HUBER, Munchen 2003, that was already mentioned in the introduction.

The radiotherapeutic effect is essentially due to through the daughter isotope of Actinium-225, namely Bismuth-213 and the Polonium-213 formed therefrom, which are particularly suitable as α-emitter for highly specific and locally restricted irradiation of tumors.

It is very advantageous if the method according to the invention can be carried out in a continuous way, as by doing so, a bigger amount of $^{226}$Ra targets for the continuous production of radioimmuno antibodies for therapeutical purposes can be produced in an industrial or semi-industrial process and as they can be stored at least for a short period of time.

In order to obtain the desired $^{225}$Ac, the radium targets obtained by the use of inventive process may then be subjected to high-energy proton irradiation, for example from 10 to 25 MeV, preferably from 18 to 23 MeV, in a cyclotron or a linear accelerator.

For the production of radionuclides themselves, it is referred to the teaching of EP 0 752 709 B1 and EP 0 962 942 A1, which are both incorporated herewith by reference.

An $^{225}$Ac thus obtained is bound for example to antibodies for radioimmunotherapy. Such procedures of coupling are well known to those skilled in the art and can be found for example in KASPERSEN et al. 1995 as well as in HUBER, 2003.

A special advantage of the radium targets according to the invention is that they exhibit basically pure radium material in their radium containing coating. Hereby, it is achieved that the targets are free of carriers or diluents, for example barium salts, which had to be added to the conventional radium targets of the prior art, i.e. the target pellets mentioned in the introduction, in order to homogenize the radium-containing material. Due to the possibility to be able to work without such carrier materials as barium compounds, the chemical separation and purification of the formed $^{225}$Ac becomes substantially more simple and the yields of irradiation are optimized, as competitive nuclear reactions, as for example those from barium nuclei, are not possible.

The present invention further comprises all combinations of all disclosed single features together, independent from their AND- or OR-linkage.

Further advantages and features can be seen from the description of the embodiments of the invention as well as from the drawings.

EXAMPLES

Example 1

Figure 1:
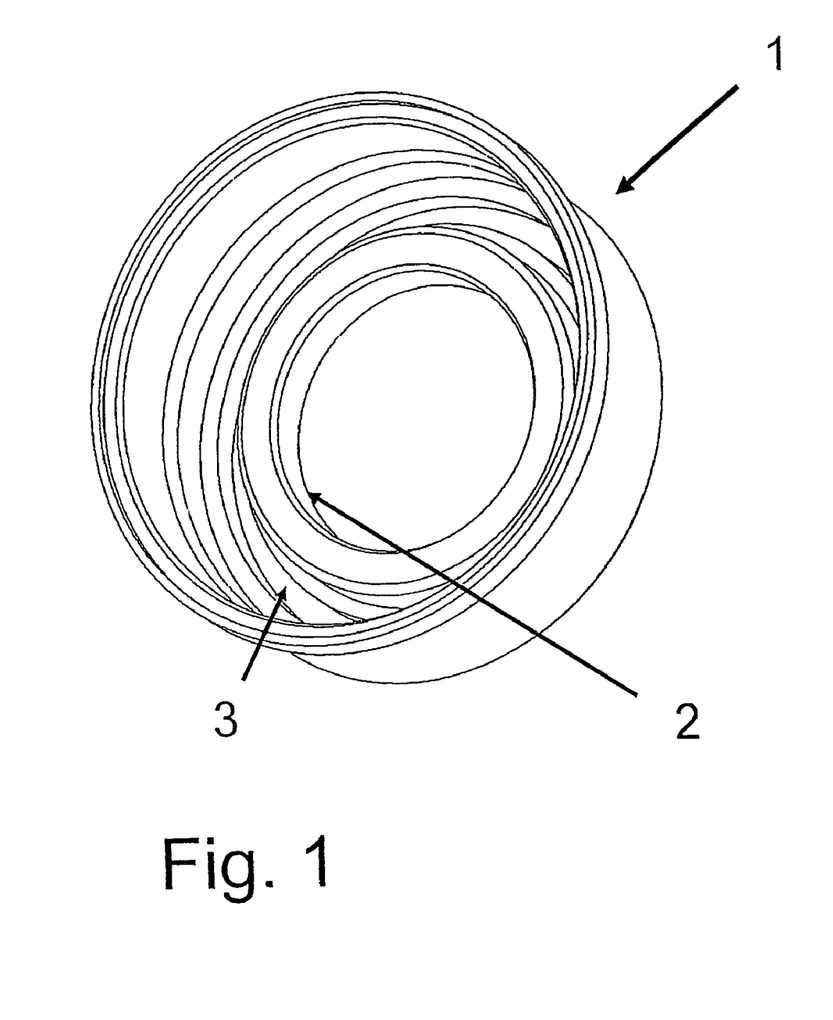
FIG. 1 shows a perspective view of a cup-shaped radium target according to the invention.

In FIG. 1 an aluminium target cup exhibiting a groove-shaped recess 3 on the outer edge of its base 2 and resembling a trench, is labelled 1.

Figure 2:
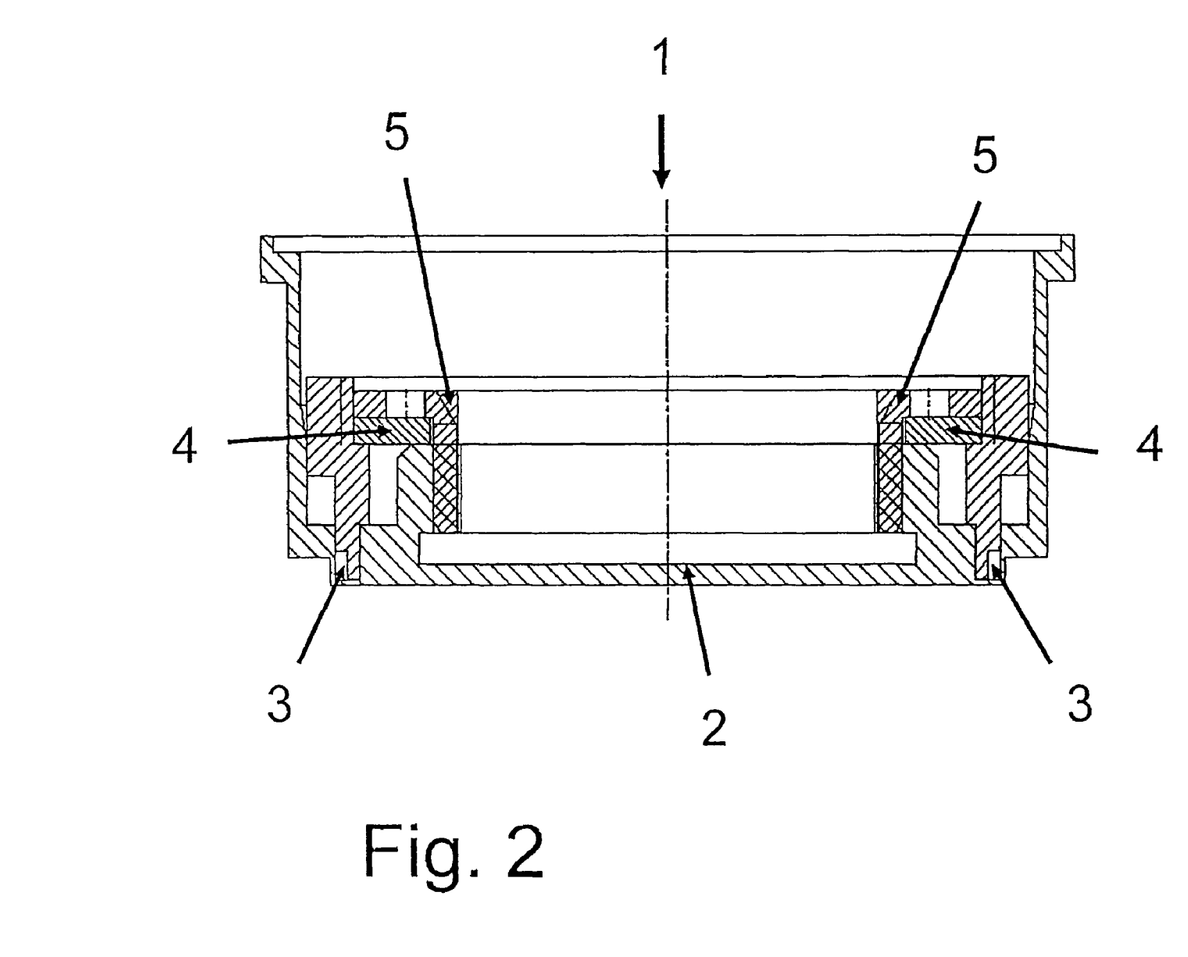
FIG. 2 shows a cross-sectional view of a radium target according to the invention.

FIG. 2 shows a longitudinal section of the target cup 1 in FIG. 1, however, with integrated centrepiece 5.

For the production of a $^{226}$Ra target, saturated radium salt iones are used (approx. 10 mg Ra per ml solution). In order to fill the groove-shaped recess 3 of the target cup 1, less than 100 ml solution are required.

The target cup 1 is arranged and heated on a rotating heating disc. Around the edge of the cup 1 a recess 3 is provided, in which the materials to be irradiated are to be introduced. The measurements of this recess 3 lie in the range of millimeters.

By means of a dispensing device for small drops (in the test, a time-pressure-dispenser for adhesives was used) a small amount of liquid is dispensed dropwise via a thin capillary (diameter approx. 0.5 mm) In our example, the distance of the end of the capillary to the base of the groove-shaped recess is kept on approx. 5 μm by means of a scanning sensor for reflected light.

The temperature of the device (80° C.) as well as the amount of drops and their frequency (2 drops per second) are coordinated in such a way that the solvent of the liquid is enabled to evaporate, whereby a uniform layer is formed.

Modifications of the device are imaginable where drops into the target cup 1 are not introduced top down, but laterally, so that the layer is formed on the inner outer wall, which is advantageous for an irradiation process in the cyclotron. Furthermore, the coating may take place with a high circumferential velocity of the target cup 1, so that the centrifugal force provides an additional compression of the material on the outer wall of the cup 1.

A further modification is to keep the target cup fixed and to rotate the dispensing device in such a way that a capillary or needle of the dispensing device charges the surface of the groove-shaped recess with radium containing material.

Afterwards, the target cup 1 having the $^{226}$Ra layer arranged on it, is, if required, dried under an infrared lamp until the weight remains constant, in order to dewater the radium containing coating as completely as possible, optionally including the crystal water.

Afterwards, the target cup 1 is weighted and the net mass of the $^{226}$Ra-containing layer is determined in order to calculate the yield.

An alternative way for supervision of the yield of the layer application is—instead of weightening—is to measure the y-activity of $^{226}$Ra on a high resolution y-spectrometry system.

After they have been sealed gasproof and waterproof, the target cups 1 thus obtained are arranged as radium targets in the proton beam of a cyclotron in order to carry out the nuclear transformation to $^{225}$Ac.

For safety reasons, the recess 3 may be covered by means of a seal 4 and a centrepiece 5—as shown in FIG. 5.

Example 2

Instead of the dropwise dispensing of the radium containing material, a liquid film for the coating of the target cup 1 of example 1 is used in the present example. A teflon needle with a diameter of 0.1 mm guided by a metal sheath serves as capillary.

The aluminium target cup 1 is being rotated, in our example it is heated to a temperature of approx. 80° C. by means of an IR irradiator that can be swayed over the cup, then the teflon needle is guided over a manipulator device to the cup 1 over the groove-shaped recess 3. The teflon needle is lowered into the recess 3, whereby the distance of the end of the needle to the base of the recess 3 is determined continuously via a scanning sensor for reflected light. The process of lowering is carried out until the desired distance—in this case approx. 5 μm—is achieved and kept constant. Afterwards, a control unit triggers the delivery of $^{226}$Ra containing material, which is pumped out of the supply vessel. The liquid hits the heated surface as a thin film, whereby the solvent vaporizes immediately and a solid overgrowth is deposited on the surface.

As soon as the temperature, which is also to be measured continuously, falls below a certain desired value, the process of coating is interrupted and the cup 1 is reheated in order to be then further coated.

When the process of coating is terminated, the aluminium target cup is transported to a further shielded part of the device, where it is sealed waterproof and gasproof and then transformed outward.

In order to guarantee the safety of the whole coating procedure, the device is formed as glovebox.

For the continuous automation of the procedure, all steps are controlled and carried out via a central control unit with sensors.

With the method according to the present invention it is possible, to obtain highly potent $^{22}$Ra targets with different $^{226}$Ra contents.

In particular, the method according to the present invention enables the deposition of layers with a good homogeneity on the aluminium-$^{226}$Ra target. This is in particular important for the irradiation of the target in the cyclotron, as the atomic nuclei of the radium are hereby subjected homogenously to the proton flux.

The use of aluminium as substrate for $^{226}$Ra offers various advantages for the irradiation in a cyclotron and the subsequent radiochemical regeneration of the irradiated target. The advantages of the aluminium lie in the nuclear physical and chemical properties of the aluminium:

Nuclear properties: Aluminium has just one single stable isotope. The activation products that are formed from the aluminium are very short-lived. The formation of only short lived radionuclides on aluminium facilitates the radiochemical purification of Ac-225 and reduces the cooling time of the target after irradiation. As the loss of energy of the protons in aluminium is very low, it is possible to use several thin films of aluminium without substantial reduction of the proton energy.

Physical properties: Aluminium is a light metal with good thermal and electrical conductivity. It is easy to handle and can be adapted easily to the required geometry.

Chemical properties: Aluminium can easily be dissolved in mineral acids and it can be easily separated from the resulting Actinium. Aluminium foils are available with a high degree of chemical purity and at reasonable prices.

In practice, it has turned out that approx. 3 to 5 g/cm$^2$ $^{226}$Ra with good adhesion may be deposited on the aluminium surface.

The method facilitates the eventual automation of the target production process. This aspect is very important for the radiation safety and the continuity of the process.

The invention claimed is:

1. A method of producing a radium target for the production of a radionuclide by means of accelerated protons, comprising:
    (a) applying at least one radium-containing material dissolved or suspended in an aqueous-organic solvent on a surface with a dispersing device in such a way that the dispersing device and the surface move relative to each other thereby producing an applied radium-containing layer, wherein the surface is the surface of a metal cylinder-shaped hollow vessel that comprises a base having an outer edge and further comprises a groove-shaped recess at the outer edge of the surface of its base; and
    (b) removing the aqueous-organic solvent from the applied radium-containing layer to generate a radium target suitable for use as a target for the production of $^{225}$Ac by means of accelerated protons.

2. The method of claim 1, wherein the metal is a metal selected from the group consisting of aluminium, copper, titanium, gold, and gold plated stainless steel.

3. The method of claim 1, wherein the radium-containing material is a $^{226}$Ra salt.

4. The method of claim 3, wherein the $^{226}$Ra salt is selected from the group consisting of a $^{226}$Ra nitrate, a $^{226}$Ra carbonate, a $^{226}$Ra chloride, a $^{226}$Ra oxide, or any combination thereof.

5. The method of claim 1, further comprising targeting the radium target with protons accelerated by means of a cyclotron or a linear accelerator.

6. The method of claim 1, further comprising a step of targeting the radium target with protons accelerated by means of a cyclotron or a linear accelerator to produce $^{225}$Ac.

7. The method of claim 1, wherein the surface is a heated surface and wherein application of the at least one radium-containing material dissolved or suspended in an aqueous-organic solvent results in substantially spontaneous removal of the aqueous-organic solvent by evaporation.

8. The method of claim 1, further comprising an additional step of:
 (a) applying at least one radium-containing material dissolved or suspended in an aqueous-organic solvent on the radium target with a dispersing device in such a way that the dispersing device and the radium target move relative to each other thereby producing a second applied radium-containing layer, and
 (b) removing the aqueous-organic solvent from the second applied radium-containing layer to generate a radium target suitable for use as a target for the production of $^{225}$Ac by means of accelerated protons.

9. The method of claim 1 or 8, wherein the at least one radium-containing material dissolved or suspended in an aqueous-organic solvent is applied by wetting the surface or the radium target by dropwise application of at least one radium-containing material dissolved or suspended in an aqueous-organic solvent.

10. The method of claim 7, wherein the wetting of the surface and/or the applied radium-containing layer takes place by the application of a thin film.

11. The method of claim 1 or 8, wherein the removing of the aqueous-organic solvent comprises evaporating the aqueous-organic solvent by heating the surface or the radium target.

12. The method of claim 11, wherein the heating is by IR radiation.

13. The method of claim 1, wherein the at least one radium-containing material dissolved or suspended in an aqueous-organic solvent is applied under reduced pressure, and the solvent is removed by evaporation.

14. The method of claim 13, wherein the evaporation under reduced pressure occurs at the reduced boiling point of the at least one radium-containing material dissolved or suspended in an aqueous-organic solvent at the reduced pressure.

15. The method of claim 1, wherein the metal cylinder-shaped hollow vessel is a beaker-shaped or cup-shaped object.

16. The method of claim 1, wherein the groove-shaped recess at the outer edge of the surface of its base has a depth of about 0.5 to about 10 mm.

17. The method of claim 16, wherein the groove-shaped recess at the outer edge of the surface of its base has a depth of about 0.5 to about 3 mm.

18. The method of claim 1, wherein the groove-shaped recess at the outer edge of the surface of its base has a breadth of about 0.5 to about 10 mm.

19. The method of claim 18, wherein the groove-shaped recess at the outer edge of the surface of its base has a breadth of about 1 to about 3 mm.

20. The method of claim 1 or 8, wherein the at least one radium-containing-material dissolved or suspended in an aqueous-organic solvent is applied in drops.

21. The method of claim 20, wherein the drops have a diameter of about 100 to about 1000 μm.

22. The method of claim 21, wherein the drops have a diameter of about 200 to about 800 μm.

23. The method of claim 22, wherein the drops have a diameter of about 450 μm.

24. The method of claim 15, wherein the at least one radium-containing material dissolved or suspended in an aqueous-organic solvent is applied from a capillary so that the base of the groove-shaped recess of the cup-shaped object is wetted and the end of the capillary is guided along in the direction of the overgrowth of coating.

25. The method of claim 24, wherein the distance between the capillary and the surface and/or the distance between the capillary and the overgrowth is detected and kept at a constant level by means of a sensor.

26. The method of claim 25, wherein the sensor is an optical sensor.

27. The method of claim 26, wherein the optical sensor is a sensor for scanning reflected light.

28. The method of claim 24, wherein the capillary comprises a hydrophobic material.

29. The method of claim 28, wherein the hydrophobic material is a fluorinated polymer.

30. The method of claim 29, wherein the fluorinated polymer is Teflon.

31. The method of claim 28, wherein the capillary comprises a stabilizing metal sheath.

32. The method of claim 1 or 8, wherein the aqueous-organic solvent comprises at least one alcohol.

33. The method of claim 32, wherein the alcohol is a linear or branched $C_1$ to $C_5$ alkyl alcohol.

34. The method of claim 32, wherein the alcohol is selected from the group consisting of ethanol, 1-propanol, 2-propanol, and mixtures thereof.

35. The method of claim 1, wherein the at least one radium-containing material dissolved or suspended in an aqueous-organic solvent comprises acetone.

36. The method of claim 1, wherein the radium-containing material is applied to the surface of an intermediate support.

37. The method of claim 36, wherein the intermediate support is aluminium foil.

38. The method of claim 1, wherein the radium-containing material is applied to the surface of an aluminium intermediate support that is placed in the cylinder-shaped hollow vessel.

39. The method of claim 1 or 8, further comprising a step of drying the radium target.

40. The method of claim 39, wherein the radium target is dried by means of IR radiation.

41. The method of claim 1 or 8, wherein the applied radium-containing layer comprises crystal water, and wherein the method further comprises a step of drying the applied radium-containing layer to remove all or substantially all the crystal water in the applied radium-containing layer.

42. The method of claim 1 or 8, wherein the at least one radium-containing-material dissolved or suspended in an aqueous-organic solvent is applied to the surface in a continuous manner.

43. The method of claim 1 or 8, wherein the at least one radium-containing material dissolved or suspended in an aqueous-organic solvent is applied to the surface under an inert gas atmosphere.

44. The method of claim 1 or 8, further comprising targeting the applied radium-containing layer suitable for use as a radium target with protons accelerated by means of a cyclotron or a linear accelerator.

* * * * *